United States Patent
Webb et al.

[11] Patent Number: 6,137,104
[45] Date of Patent: Oct. 24, 2000

[54] FAST AUTOMATED SPECTRAL FITTING METHOD

[75] Inventors: Christopher Webb, Los Altos, Calif.; Philip V. Wilson, Mount Waverley, Australia

[73] Assignee: Varian, Inc., Palo Alto, Calif.

[21] Appl. No.: 09/158,648

[22] Filed: Sep. 22, 1998

Related U.S. Application Data
[60] Provisional application No. 60/089,148, Jun. 12, 1998.

[51] Int. Cl.$^7$ ............................................. G01J 3/50
[52] U.S. Cl. ..................... 250/226; 250/208.1; 356/346
[58] Field of Search ................... 250/226, 208.1, 250/576, 461.2, 339.07; 356/346, 300, 349, 326; 126/665

[56] References Cited

U.S. PATENT DOCUMENTS

| | | | |
|---|---|---|---|
| 5,308,982 | 5/1994 | Ivaldi et al. | 250/339.01 |
| 5,596,407 | 1/1997 | Zander et al. | 356/328 |
| 5,784,162 | 7/1998 | Cabib et al. | 356/346 |

FOREIGN PATENT DOCUMENTS

| | | |
|---|---|---|
| 0 502 495 | 9/1992 | European Pat. Off. . |
| 0 560 006 | 9/1993 | European Pat. Off. . |

OTHER PUBLICATIONS

Article by van Veen et al., entitled *"Kalman filtering of data from overlapping lines in inductively coupled plasma-atomic emission spectrometry,"* published in *Spectrochimica Acta* in 1990, in vol. 45B, No. 3, pp. 313–328. (Month Unknown).

Article by Karstang et al., entitled *"Multivariate Prediction and Background Correction Using Local Modeling and Derivative Spectroscopy,"* published in *Anal. Chem.* in 1991, in vol. 63, pp. 767–772. (Month Unknown).

Article by Sasaki et al., entitled *"Estimation of component spectral curves from unknown mixture spectra,"* published in *Applied Optics in 1984*, in vol. 23, No. 12, pp. 1955–1959. (Month Unknown).

Article by Tahboub at al., entitled *"Evaluation of Multiwavelength First– and Second–Derivative Spectra for the Quantitation of Mixtures of Polynuclear Aromatic Hydrocarbons,"* published in *Anal. Chem.* in 1985, in vol. 57, pp. 38–41. (Month Unknown).

Article by Bauer et al., entitled *"Selectivity and error estimates in multivariate calibration: application to sequential ICP–OES,"* published in *Spectrochimica Acta*, in 1991, in vol. 46B, No. 8, pp. 1185–1196. (Month Unknown).

Article by Thomas et al., entitled *"Comparison of Multivariate Calibration Methods for Quantitative Spectral Analysis,"* published in *Anal. Chem.* in 1990, in vol. 62, pp. 1091–1099. (Month Unknown).

*Primary Examiner*—Que T. Le
*Attorney, Agent, or Firm*—Edward H. Berkowitz

[57] ABSTRACT

A spectral interval excited by ICP-ES containing expected lines is modeled from wavelength calibration information and from spectra of model components. A sample is then excited and fit to the data with concurrent observation of wavelength calibration and a linear least squares fit obtained with analysis of residuals to determine presence of unexpected spectral features which, if present, provide additional model components for an iterative fitting.

8 Claims, 6 Drawing Sheets

FAST AUTOMATED SPECTRAL FITTING METHOD

This application claims benefit of Provisional Appl. 60/089,148 filed Jun. 12, 1998.

FIELD OF THE INVENTION

The invention relates to the practice of quantitative evaluation of the components of spectral distributions and particularly to the automated analysis of spectra.

BACKGROUND OF THE INVENTION

The evaluation of spectral distributions has been highly developed over many decades in conjunction with the various spectroscopies which have evolved. In the context of analytic instruments, the positions of spectral lines to be observed is substantially known a priori and it is the relative concentration of the elements present which is to be determined. Positions of expected lines may be perturbed slightly by instrumental effects or by the superposition of proximate lines. At high resolution, line spectra exhibit lineshapes which may be studied by fitting techniques to reveal the quantitative presence of partially overlapping lines.

In the case of certain specific modern spectroscopic instruments the data is photo-electronically accumulated at discrete positions (pixels) with the result that a narrow peak may be defined by only a few datums. Given the discrete nature of the photoreceptive pixels, finite resolution and dispersion of the instrument and possible instability of the instrument to drift, peak position and drift may be determinable as fractional pixel quantities. The spectral evaluation technique of the present invention accommodates this combination of circumstances.

In the particular case where atomic emission spectra are excited from an inductively coupled plasma, the nature of ICP excitation is such that the density of spectral lines is quite high compared to more sedate excitation. Thus, interferences are frequently encountered.

In the prior art, spectral decomposition from ICP-AES has been discussed by van Veen et al., Spectrochimica Acta, v.45B, pp.313 (1990). The method reported there is based upon a Kalman filter technique with the consequence that this prior art procedure is iterative and further requires multiple data acquisitions to examine wavelength shifts. This particular work was accomplished with a scanning type instrument arranged to yield a far greater density of points for peak definition than would ordinarily be available in a broad range instrument with discrete detection elements for the simultaneous acquisition of data over a wide spectral range. Quite apart from the nature of the particular spectroscopic instrument, the spectral treatment as described, is very intensive in computation and time required therefore.

Another approach to spectral decomposition of ICP-AES data is described in U.S. Pat. No. 5,308,982 to Ivaldi, et al. This procedure employs a first (and preferably second) derivative of the spectrum in process to construct a model spectrum which conforms to the observed spectrum by adjustment of appropriate parameters, thereby yielding concentration information. Such methods are practiced at the price of a significantly diminished signal to noise parameter.

In the present work, ICP-AES is carried out in an instrument which is described in U.S. Pat. No. 5,596,407, incorporated by reference herein. This instrument includes an electronic focal plane detector characterized by sequences of discrete pixels arranged in continuous linear arrays.

SUMMARY OF THE INVENTION

The invention expresses an expected spectral interval in an analytic form and by linear least squares techniques, extracting the coefficients of concentration for the elements represented by lines excited during ICP-AES. Plasma gas and standards yield data from which wavelength calibration, concentration calibration and line shapes are obtained for analytical representation of the spectral interval of interest. Wavelength shifts, in the nature of translation of the calibration are monitored at each sample data acquisition. Any shift detected in the calibration causes a corresponding shift in model components employed to realize the analytical representation. Unexpected spectral features in proximity to peaks of interest are detected from the residuals of the fitting procedure and the presence thereof leads to an iteration wherein a model component (peak) is shifted to form an additional model component for which the fitting operation is repeated. Such features which are located sufficiently far from peaks of interest are masked from further analysis.

DETAILED DESCRIPTION OF THE INVENTION

The functional structure of the invention may be seen as comprising two phases: building the (expected) spectral model, and analyzing the observed spectrum.

Figure 1A:
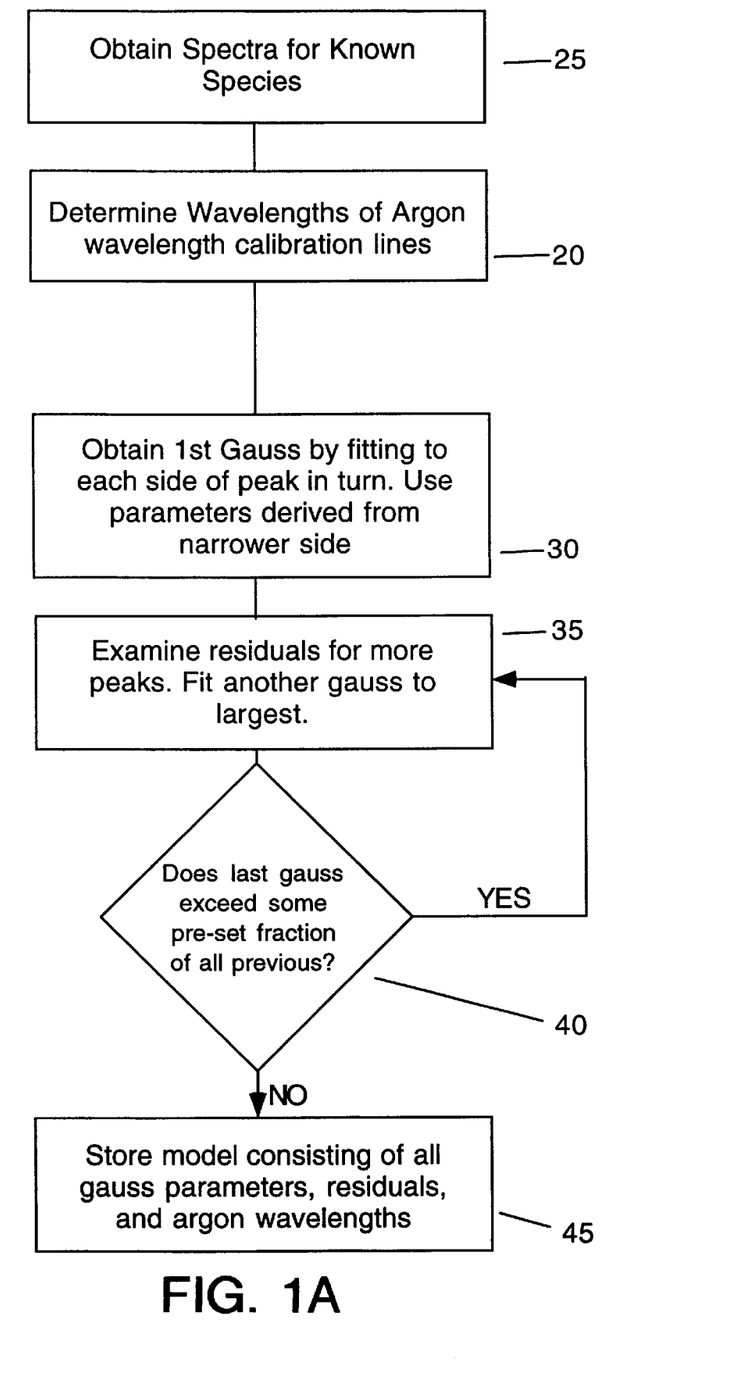
FIG. 1A shows in schematic form the steps of the model building phase of the invention.

The model building phase, schematically illustrated in FIG. 1A, has the goal of expressing the expected spectrum as an analytic representation, e.g., as a sum of gaussians together with slowly varying residuals. The invention is not limited to use of a gaussian form (one may employ lorentzian or other appropriate forms), but reference will be made to gaussian functions, both as a preferred and a generic choice. Model building should be regarded as inclusive of the straightforward referencing of standard wavelengths to the instrument through observation 20 of characteristic spectral lines of the plasma gas including the sample. Typically argon is employed for the purpose of supporting the plasma and references to argon should be interpreted to include any alternate choice for the plasma gas. Selected calibration lines are smoothed during this step 20 (for example using a well known procedure such as the Savitsky-Golay smoothing filter, -see A. Savitsky and M. J. E. Golay, Analyt. Chem., v. 8, p.1627, 1964 and J. Steiner, Y. Temonia and J. Deltour, ibid., v.6, p.1906, 1972) and then the three highest amplitude points of a calibration peak are fit to a quadratic to extract the peak maximum coordinate of wavelength. The combination of these two procedures was found to achieve excellent accuracy with overall computational simplicity. Expressed in pixels of a discrete focal plane detector, it has been confirmed that this method yields results which agree (typically within much less than 0.1 pixel) with computationally more intense non-linear fitting procedures, It should also be noted that this combination of steps, the Savitsky-Golay filter effectively fits a polynomial (using 3 points) to the data points. The subsequent quadradic fitting is therefore well matched to this step. Use of a greater number of points would be largely redundant. It was confirmed using this procedure for a group of peaks over a wide range of wavelengths that shifts with respect to an argon calibration line at 419.832 nm could be corrected to better than 0.1 pixels.

During the model building phase, one separately calibrates the intensity scale against spectral lines from standard sources of known concentration by introduction of known standard(s) for spectral acquisition and recording 25. The procedure 30 for fitting an observed set of points, constituting a peak, consists of fitting observed points on each (roughly) one half of the peak separately to the selected (preferably, gaussian) shape. That is, the data comprising a peak is treated as comprising two statistically similar portions. Various ways of making this division are acceptable. The portions may be chosen to exhibit roughly equal area for example, or a maximum point (if there is one) may be treated as common to the two portions for fitting purposes. From the separate fits, there is extracted corresponding width and peak position parameters. The peak position corresponding to the narrower width is selected to represent the model spectral component for the respective spectral feature. This permits a systematic treatment for peaks which may exhibit an asymmetry for any of a variety of reasons and minimizes the number of gaussians ultimately required to form the model. It is advantageous to construct a model including two closely overlapping peaks from the same element. An example is the case of thallium near 190 nm. In such case, the larger peak is matched first and the residual are analyzed 40 to determine the presence of additional spectral features. The residuals containing the second peak data are fit subsequently. Asymmetry may result from some instrumental influence or from a standard which contains multiple peaks in extremely close proximity. The selected shape (typically, gaussian) together with the residuals now represent the (possibly asymmetric) model function associated with the particular peak wavelength.

Analysis of residuals 40 concludes with the determination that the residuals meet some predetermined criteria for goodness of fit. At the model building phase, iteration is terminated when the fitting of a secondary or tertiary gaussian provides a component having less than some selected fraction (for example 0.1 in area) compared to the primary gaussian.

Figure 1B:
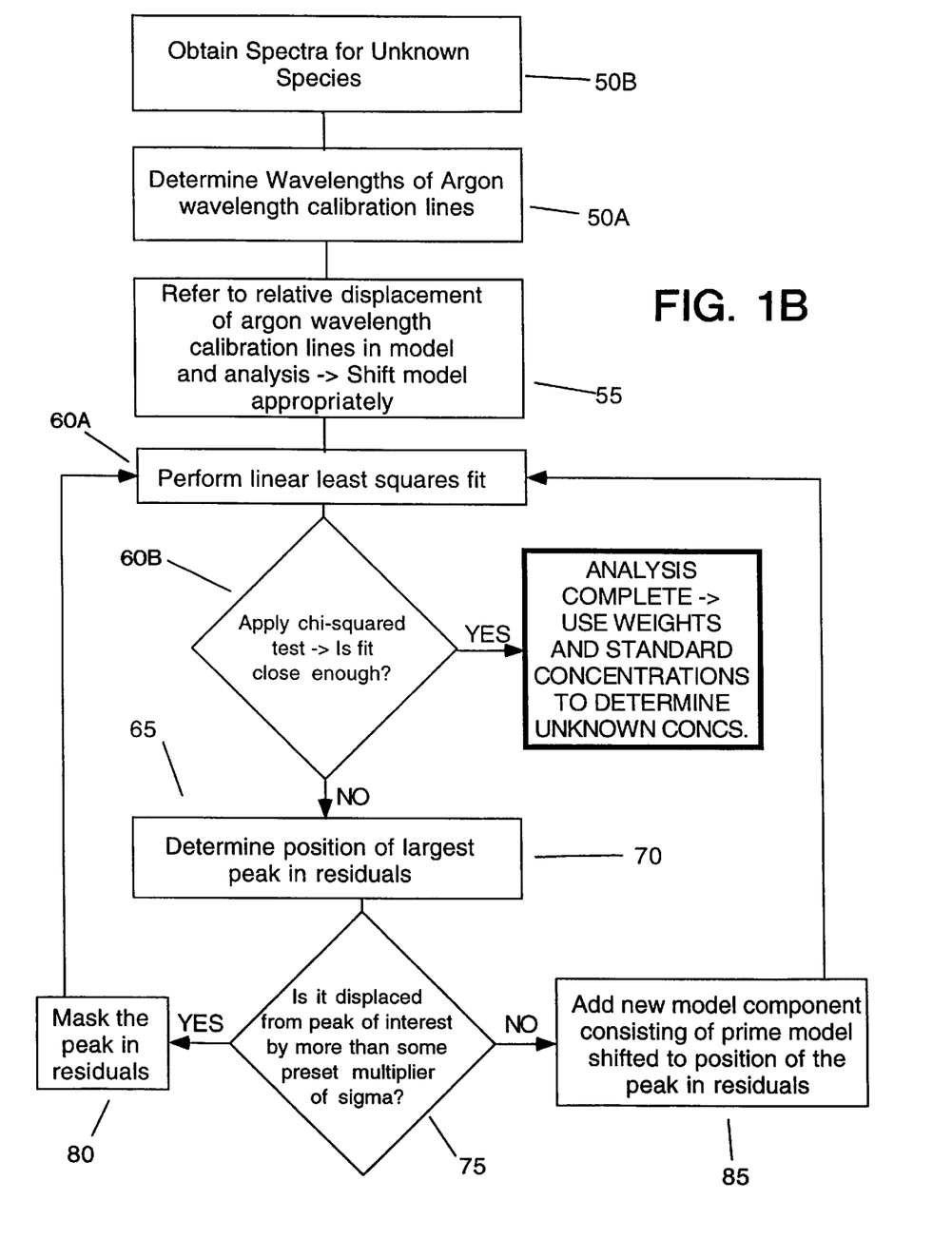
FIG. 1B shows in schematic form the steps of the analysis phase of the invention.

The second phase of the procedure, as schematically shown in FIG. 1B, is the analysis where each spectral interval or window, containing spectral features of interest excited from an uncontrolled sample, is observed (together with observation 50 of wavelength calibration lines). Stored calibration data from the proceeding model building phase are compared with currently observed calibration line(s) in order to monitor potential instrumental drift at step 55. Such drift may arise, for example, from local heating of the instrument with consequent mechanical distortion or expansion/contraction affecting optical paths. Differences in position of calibration wavelength(s) on the focal plane of the instrument define a displacement which redefines the positions of the model functions. The spectral interval is then represented by model functions and background representation (if any) which are explicitly corrected to express the drift by a shift in the (fractional) pixel location and the concentration coefficients. Observed wavelength drift is used to re-define the wavelength-pixel calibration and the corrected value is employed with the stored wavelength dependent spectral representation. The method of performing the shift of each model components to re-calculate the model from its component function (gaussian) and residues. The gaussian(or other function) is simply re-computed as $f^{new}(x+\Delta)=f^{old}(x)$ for a shift of $\Delta$. The residuals are shifted by the method of linear interpolation whereby the new residual function is is evaluated at each required point assuming a linear variation of the residual function in the interval comprising the two adjacent measured (pixel) values.

The concentration coefficients are extracted in the usual manner 60 of linear least squares analysis. Briefly, one represents a measured spectral interval y(x) over a wavelength interval x as $$y(x) = \left\{\sum_{k=1}^{M} a_k X_k(x)\right\} + \varepsilon(x) \qquad \text{Eq. 1}$$

where the X's represent basis or model functions and are selected functions of the variable x. These basis functions may include such choices as gaussians to represent peaks and polynomial or other appropriate form to represent background or like continuum. The residuals $\varepsilon(x)$ express the departure of the observed data from the model. One seeks to obtain the coefficients $a_k$. The well known procedure consists of forming the N×M matrix A where N is the number of values of the variable x for which measurements are obtained and M is the number of basis functions employed. The elements of A are the model functions evaluated at the wavelength shifted pixel locations $$A_{ij}=X_j(x_i) \qquad \text{Eq. 2}$$

The criteria of least squares is employed to extract the elements of the array, e.g., minimization of the quantity.

$$\sum_{i=1}^{N}\left[y(x_i) - \left\{\sum_{k=1}^{M} a_k X_k(x_i)\right\}\right]^2 \qquad \text{Eq. 3}$$

Minimization of the above expression is recognized as yielding residuals of magnitude small compared to the modeled spectra. In the present invention, the distribution of these residuals is analyzed for structure of significance, for example, forming a statistically significant peak. The displacement of any such resulting peak in the residuals is considered. If a disturbance in the residuals is sufficiently far from the peak(s) of interest within the spectral window, this region may be masked out from the analysis. That is, the measured data in this region may be excluded from the least squares fit. Should such residual peak be sufficiently proximate the peak(s) of original interest, an additional model function is assumed for the position of the residual peak and the analysis in either instance is repeated. Distant and proximate are judged on the scale of units of standard deviation, $\sigma$. The determination of significance of residuals is determined using chi-square analysis of the residuals as indicated at step 65. The details of chi-square analysis are well known and may be found in many standard works, for example, W. H. Press, S. A. Teukolsky, W. T. Vetterling, B. P. Flannery, "Numerical Recipes in C", p. 659–661, Cambridge University Press, $2^{nd}$ ed. (1992). Following the usual prescription, a goodness of fit parameter is given by minimization of the quantity $$x^2 = \sum_{i=1}^{n} \left[ \frac{y_i - \sum_{k=1}^{m} a_k X_k(x_i)}{\sigma_i} \right]^2$$

The value so determined must be compared with a reference value $\chi^2_{ref}$ to determine the acceptability of the fit. The quantities $\sigma_i$ are values of a weighting parameter which is preferably given as the product of two variables which may be termed RSD and SIG. RSD is preferably obtained by defining a number $N_p$ of contiguous points forming a window. Each set of $N_s$ contiguous points within the window, $N_p >> N_s$, is examined to find the minimum relative standard deviation of such set (for example, each 5 contiguous points in a 21 point window interval). RSD, for all values of i, is then set equal to this local minimum value, or an appropriate value, such as 0.02, whichever is larger. These choices are dependent upon the noise present in the data. If one expects to obtain about 1% accuracy for the sum of 4 pixels, then 2% for individual pixels should suffice.

The quantity SIG is determined separately for each i and is taken as the electronically offset corrected maximum signal level in proximity to the peak of interest, or alternatively, it is taken as the actual signal level at $x_i$, whichever is larger. Thus in the presence of a significant interference peak, the criteria of best fit will be governed by the peak of interest rather than the interference peak.

The evaluated quantity $\chi^2$ must be compared to a reference value. It is common to refer to standard tabulations, for example, W. Mendenhall, *Introduction to Probability and Statistics*, Duxbury Press, or to *Numerical Recipes in C*, op.cit. It is also common to estimate the reference value by multiplication of a value near unity with the number of degrees of freedom present in the data. In the present work, the number of degrees of freedom is taken as equal to the number of (unmasked) data points less the number of model components (including points used to fit any background). It is preferred, where the number of model components, apart from background, is one, to use 3 times the number of degrees of freedom as the multiplier. This relaxation of the fitting criteria has been found to yield acceptable fit parameters; otherwise, the multiplier is taken as 1.5. The test of the residuals against a reference (preferably chi-square derived) may then terminate the procedure (65). Properties of the standard samples employed yield absolute measurements in accord with known methods.

During the analysis phase, the result of statistically significant residuals leads to an iterative set of steps as outlined above for the model building phase. A single peak in the residuals is located (70) and its proximity to the major peak is ascertained (75). If the residual peak is sufficiently far from the peak of interest, there is no "interference" and these residuals may be masked out (80) from further analysis. If an interference condition is determined, then the (nearest) model peak is shifted by the indicated wavelength interval to match the residual peak position and treated as an additional model component to represent the unexpected interference (85). The least squares fit procedure is then re-entered with the new (additional) model component included in the fitting constraints.

Although the method of determining the required wavelength offset using an argon line is found adequate for the present invention in most circumstances, alternative embodiments are possible, and may be desirable in some cases. For example, a particular line-rich sample may cause an interference on that argon line ordinarily used for the wavelength reference in the spectral interval of observation, or some unusual source of wavelength drift might occur which is not uniform across the focal plane. To cope with this situation a more robust but more complicated embodiment is appropriate.

A group of argon lines is observed and the scatter in the indicated shifts monitored. That is, each of these lines is compared to its corresponding previous pixel value to establish a corresponding shift and the average and standard deviation of these shifts. If the scatter (standard deviation) exceeds some amount, say 0.1 pixels, we employ an alternative method for deriving the value of the shift to be applied to spectral modeling and analysis.

(a) Evaluate the group of argon lines for outliers, and reject the one, or some small number which are furthest removed from the average indicated shift and employ those remaining if their scatter is sufficiently small to establish an adopted value for the shift.

Another alternative is to (b) Switch immediately to a "bootstrapping" methodology. The technique employed is to search the focal plane region adjacent to the line of interest. Additional information identifying the principal elements present in the sample is required. This information is either (i) solicited from the user or (ii) derived from some other intelligent software (the nature of which is outside the scope of the present work).

Next, for the focal plane region adjacent to the peak of interest, each line there detected, is correlated with a comprehensive wavelength database, for example, a wavelength database containing over 30,000 lines observable with excitation via inductively coupled plasma. Filters are applied to the database to search only those lines in a small "cell" surrounding the line of interest and which belong only to those elements which have been determined by either (i) or (ii) to be present. If a peak is located in the region of interest and which lies within some tolerance (for example, 8 picometers or a value which is allowed to increase linearly with wavelength) of a line in the database, the two are associated and an observation error determined. Such drift measures are obtained for preferably a large number of lines (which may be done conveniently in a line-rich environment). An average drift value is determined from all the lines for which associations are possible. Some chance associations can occur which are not correct, but with proper choice of tolerance and good calibration starting point, this number will be relatively small and contribute randomly to the average which is formed. Given a sufficiently large number of lines contributing to the average, an accurate measure of drift is obtained.

Illustrative examples of the invention in use are shown in the following tables and FIGS. 3 through 6.

Boron/Iron lines near 249 nm form a well known interference, and data were obtained for evaluation with the invention. A strong memory effect is exhibited by boron; this was reduced by changing the transfer tubing between the spray chamber and torch to Teflon lined tygon. It at first appeared that the "boron" peak still accompanied the pure Fe solution even when reduced to negligible proportions for the blank. It was verified from wavelength databases that another Fe peak is expected with near the observed intensity nominally only about 1 pm away from the B peak; the somewhat crowded spectral region is given in Table 1.

TABLE 1

B/Fe lines in the spectral region of interest.

| el. | WL/nm |
|---|---|
| Fe | 249.782 |
| B | 249.773 |
| Fe(weak) | 249.772 |

The presence of the second Fe peak is not a problem for a 2-component fit where the Fe response is modeled but does represent a severe test for the unexpected interference protocol.

Two sets of data—referenced by "P" and "Q"—were obtained for various pure and mixed B/Fe solutions. The two sets differed in that a simulated wavelength drift was induced between them by a deliberate adjustment of instrument alignment. Further the difference was chosen to be about 0.5 pixels; i.e. as difficult as possible for compensation by the calibrating Ar peak. B and Fe models were created from set P, and data from both sets P & Q processed with the same models. The results are summarized in the tables 2 & 3 for 2-component and 1-component fits respectively.

TABLE 2

2-component model

| Fe conc./ppm nominal | B conc./ppm nominal | B conc./ppm Present invention | 0.5 pixel shift | ref. |
|---|---|---|---|---|
| 100 | 0.1 | 0.10 | no | P2 |
| 100 | 0.2 | 0.21 | no | P2 |
| 100 | 0.5 | 0.53 | no | P2 |
| 100 | 0 | −0.01 | yes | Q2 |
| 100 | 0.1 | 0.10 | yes | Q2 |
| 100 | 0.2 | 0.21 | yes | Q2 |
| 100 | 0.5 | 0.49 | yes | Q2 |

Figure 2:
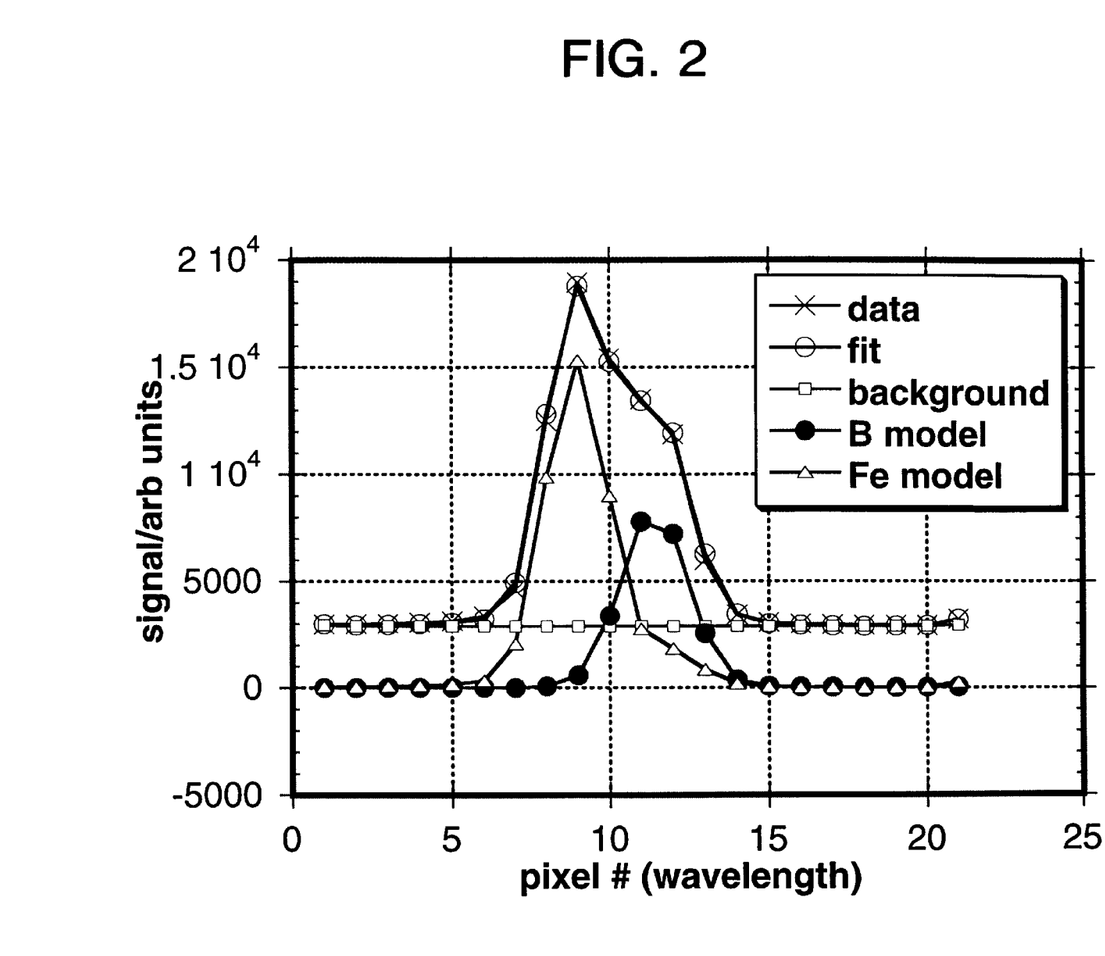
FIG. 2 is a 2 component fit, without drift, for a B—Fe test sample.
Figure 3:
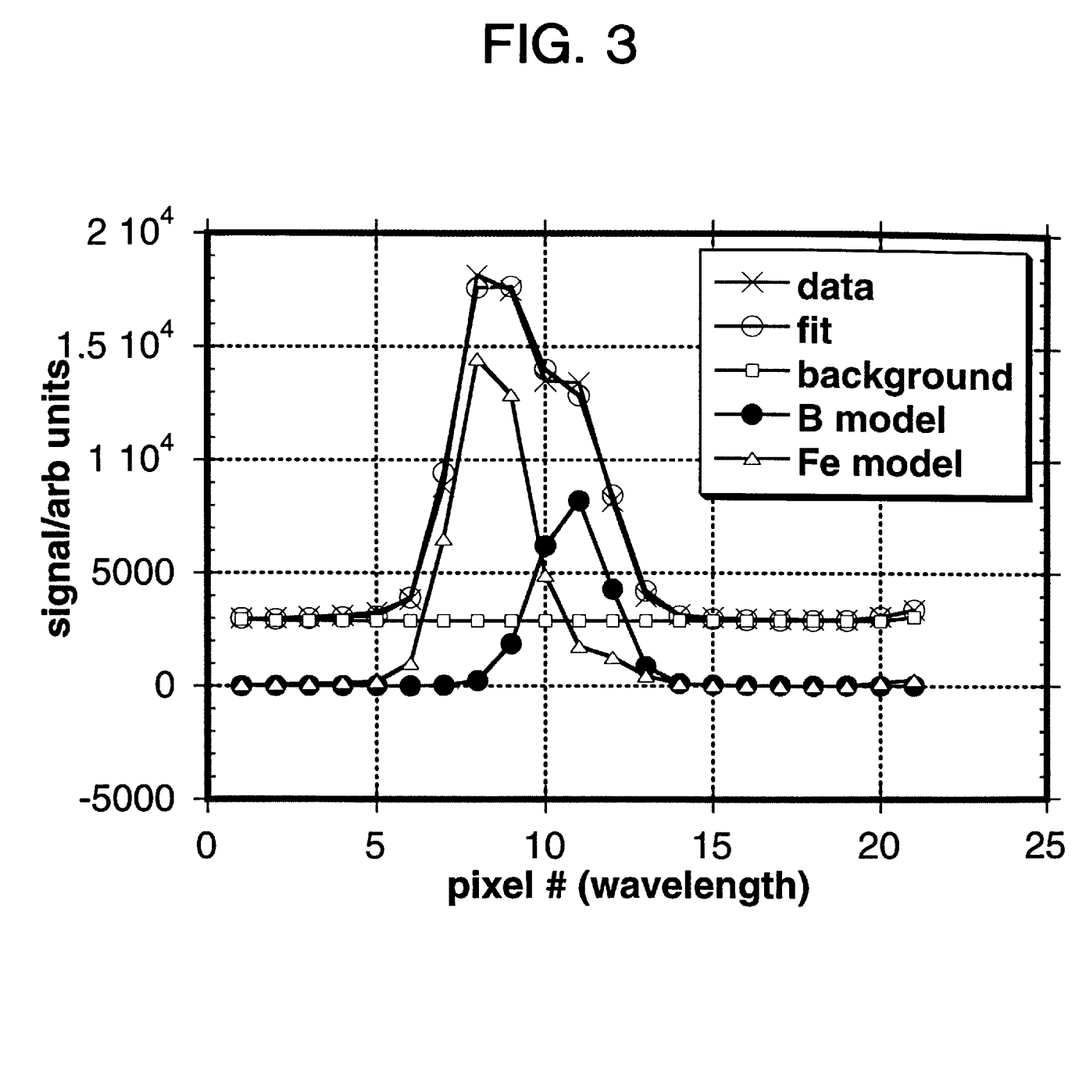
FIG. 3 is a 2 component fit, with actual 0.5 pixel drift, for a B—Fe test sample

Results of the fitting method are obtained in table 2 as described in text and shown in FIGS. 2 and 3. Reference P2 refers to data set P processed using 2 model components. A 2-component fit refers to a fitting procedure where data obtained from both pure B and Fe solutions are used to model the mixed solution data.

TABLE 3

1-component model

| Fe conc./ppm nominal | B conc./ppm nominal | B conc./ppm Present Invention | 0.5 pixel shift | ref. |
|---|---|---|---|---|
| 100 | 0 | 0.00 | yes | Q1 |
| 100 | 0.1 | 0.11 | yes | Q1 |
| 100 | 0.2 | 0.24 | yes | Q1 |
| 100 | 0.5 | 0.52 | yes | Q1 |

Figure 5:
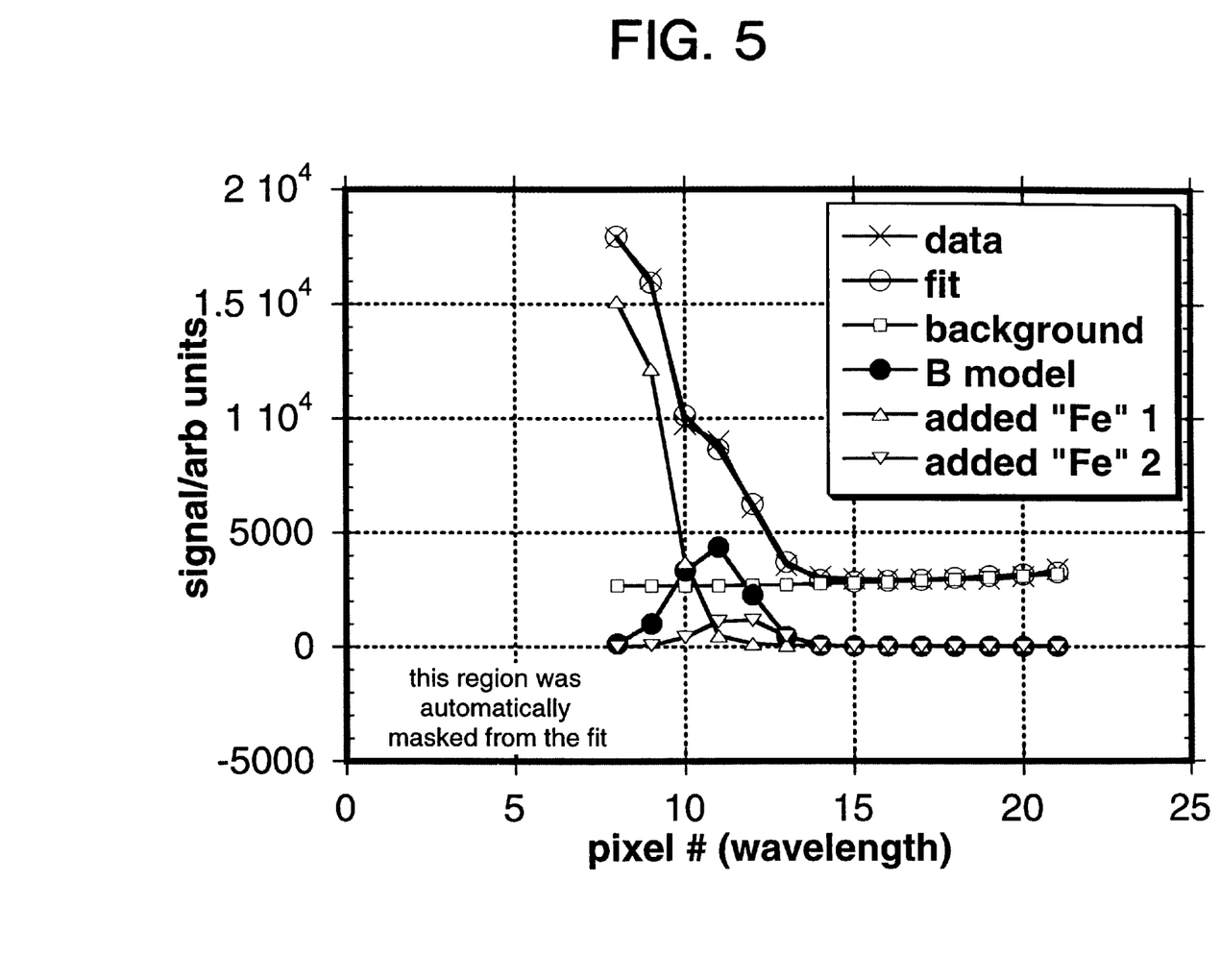
FIG. 5 is a 1 component fit to a Fe:B (1000:1) sample with 0.5 pixel drift.

Results of fitting as described in text and shown in FIGS. 5 and 6. A 1-component fit refers to a fitting procedure where only the B model is provided and the present inventive procedure detects and compensates for Fe as an "unexpected interference".

Accuracy in most cases was better than 3% for the mixed solutions with the 2-component model. Precision was typically ~1%. FIG. 3 shows the actual spectral fit in the case P2 characterized by 0.2 μg/ml B concentration, no 0.5 pixel shift between models and data and an Fe model employed for the fit. Models of both B and Fe are supplied during the fit and there is no relative shift between models and data in this case.

Figure 4:
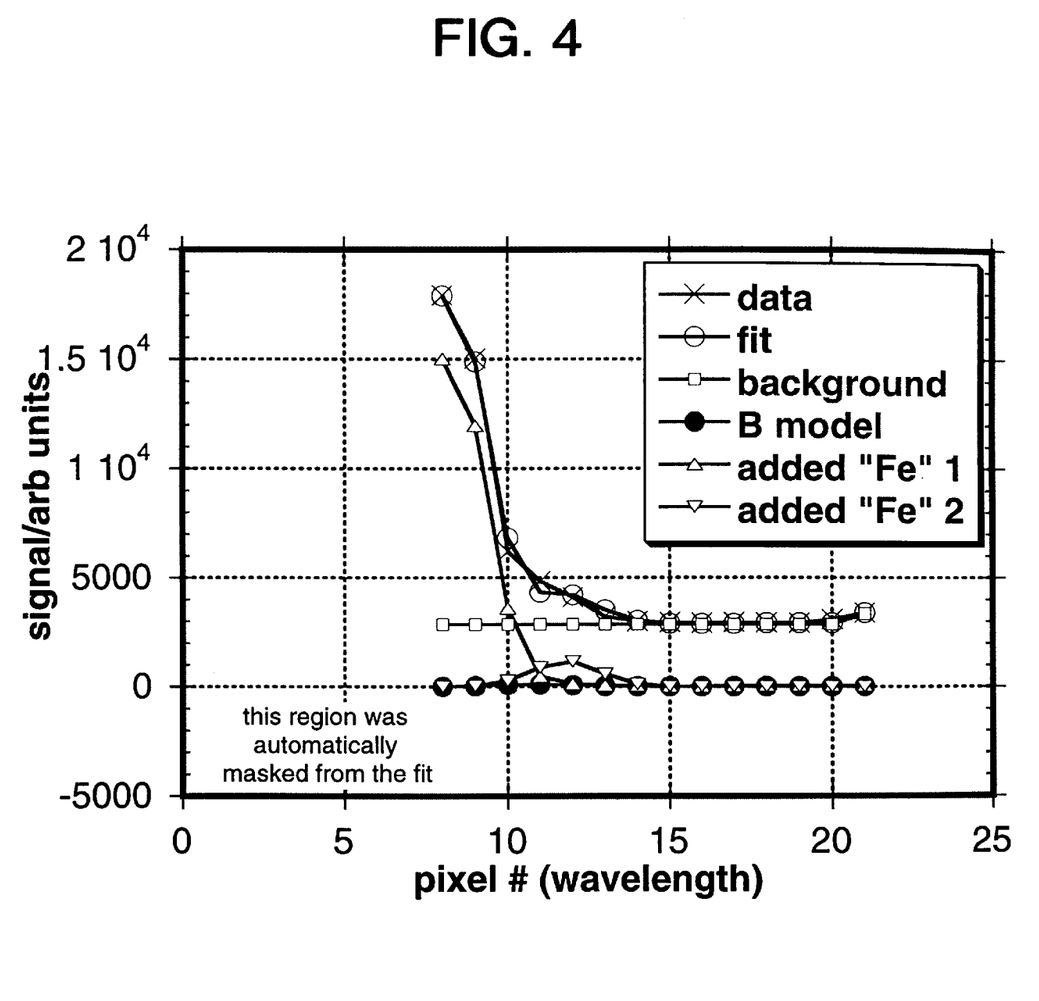
FIG. 4 is a 1 component fit to an Fe sample with 0.5 pixel drift.

FIG. 4 shows the same sample, but now with the 0.5 pixel shift between models and data (ref. Q2). Models of both B and Fe were supplied during the fit and there was a relative shift between models and data of ~0.5 pixels in this case.

The fit is slightly less accurate when the models have been shifted by the 0.5 pixel amount, but the derived concentration is identical (see Table 1). Note that if the 0.5 pixel shift is ignored, then a gross error in derived concentration occurs (>30%).

The one component model—given the near exact overlap of the second weaker Fe peak—yields results better than expected. It may be the case that the overlap is not as exact as suggested by standard wavelength databases, since for the 0 and 0.1 μg/ml B solutions a second unexpected interference was detected at a slightly larger separation than the 1 pm mentioned. The second peak was not inferred for higher concentrations, however, and this is reflected in the higher B concentrations determined (see Table 3).

The 1-component case with zero B concentration i.e. only Fe present, is shown in FIG. 5, where a spectral fit results for the case reference Q1 with 0 μg/ml B concentration. Only the B model is supplied during the fit and there was a relative shift between models and data of ~0.5 pixels in this case. This is a particularly exacting test and the spectrum is accurately interpreted as containing essentially no B. The automatic procedures built into the peak fitting procedure determine whether the fit is satisfactory at each stage (where the largest unexpected residual peak has been fitted). The procedure then either adds a new component based upon a shifted model component or a spectral region may be masked from the fit when such spectral region is too far removed from the peak of interest to be of significance. This test would defeat the prior art procedures where the models are automatically shifted according to the data and any unexpected interference is essentially fatal.

FIG. 5 shows the case similar to that in FIG. 4 but in this instance the sample includes 0.1 μg/ml B. Only the B model is supplied during the fit and there was a relative shift between models and data of ~0.5 pixels.

Although the present invention has been described with reference to particular means, materials and embodiments, from the foregoing descriptions, one skilled in the art can ascertain the essential characteristics of the present invention and various changes and modifications may be made to adapt the various uses and characteristics thereof without departing from the spirit and scope of the present invention as set out in the claims which follow.

What is claimed is:

1. A method for treatment of spectra observed on the focal plane of an optical spectrometer wherein spectra are excited by inductively coupled plasma processes, comprising the steps of
    (a) forming a representation for expected features in a predetermined spectral interval,
    (b) locating at least one first selected wavelength corresponding to a position on said focal plane, whereby a wavelength reference is established over said predetermined spectral interval on said focal plane,
    (c) observing at least one predetermined spectral feature having a known concentration, whereby a scale of concentration is established,
    (d) representing each said spectral feature by the combination of a selected mathematical form dependent upon wavelength and the residuals realized by comparison of said form and said observed spectral feature whereby a model spectral component is obtained,
    (e) analyzing a sample, (f) recording the spectra of said sample at least within said spectral window and simultaneously therewith observing again said at least one first selected wavelength, (g) determining any shift in location on said focal plane for said first selected wavelength as obtained at step (b) compared to step (f) and incorporating any said shift in each said model spectral component by transforming said mathematical form and said residuals accordingly, (h) performing a linear least squares fit of said recorded spectra to said model spectral components whereby the intensity of spectral features corresponding to said model components is established together with the distribution of residuals resulting therefrom, (i) analyzing said residuals and determining whether said fit meets predetermined criteria for terminating said treatment, and in default thereof, (j) inspecting said distribution of residuals to determine whether a significant residual maximum is located therein and in response thereto,
- locating the wavelength corresponding to said residual maximum and defining another model component located at the wavelength of said residual maximum and repeating steps (h) and (i), or,
- where no significant residual maximum is located, displaying said intensity and terminating the treatment.

2. The method of claim 1 wherein said step of representing each said spectral feature comprises treating each spectral feature forming a peak as comprising two portions of similar statistical significance, separately fitting the portions to a selected function, and selecting that fitting corresponding to the more narrow of the two fits as an initial representation of said peak.

3. The method of claim 2 wherein either of said portions includes the residual maximum of said peak.

4. The method of claim 1 wherein said step of locating comprises applying a smoothing filter to data in said spectral interval and performing a quadratic fit to the three most prominent datums whereby said wavelength is located.

5. The method of claim 4 wherein said step of locating further comprises selecting wavelengths corresponding to prominent spectral features attributable to a plasma gas of said inductively coupled plasma.

6. The method of claim 5 further comprising establishing the integrity of said selected first wavelength, comprising locating additional said wavelength references attributable to said plasma gas and subsequently observing each said wavelength reference spectral features and deriving the corresponding apparent shift in the position thereof, and determining whether the consistency among said derived shifts indicates the presence of an interference affecting at least one said first and additional wavelength reference spectral feature.

7. The method of claim 6 wherein the aggregate of said derived shifts is treated to obtain the expected statistical variance in the aggregate of said derived shifts, disregarding any one of said aggregate deviating from the average thereof by more than said expected statistical variance, re-determining the average value of said derived shift and adopting said re-determined value for said step (g).

8. The method of claim 1 wherein said step of transforming comprises shifting said mathematical form by said shift determined at step (g) and linearly interpolating the residuals as determined at step (d) by said shift.

* * * * *